US00PP07889P

United States Patent [19]

Zaiger et al.

[11] Patent Number: Plant 7,889

[45] Date of Patent: Jun. 23, 1992

[54] NECTARINE TREE 'ARTIC ROSE'

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 624,691

[22] Filed: Dec. 5, 1990

[51] Int. Cl.[5] ..... A01H 5/00

[52] U.S. Cl. ..... Plt./40

[58] Field of Search ..... Plt./40, 41

*Primary Examiner*—James R. Feyrer

[57] ABSTRACT

Our new and distinct variety of nectarine tree has the following unique combination of desirable features:

1. Heavy and regular production of fruit.
2. Fruit with firm white flesh having good handling and shipping ability.
3. Fruit that will hold firm on the tree 5–7 days after tree ripe.
4. Fruit with excellent flavor and eating quality.
5. Relatively uniform ripening of the fruit on the tree.
6. Vigorous upright growth of the tree.

1 Drawing Sheet

ORIGIN OF THE VARIETY

Our new variety of nectarine tree was originated by us in our experimental orchard located near Modesto, Calif. as a third generation seedling of a cross between Ruby Gold Nectarine (U.S. Plant Pat. No. 3,101) and Red Wing Peach (U.S. Plant Pat. No. 621). We grew and maintained a large group of these third generation seedlings under close observation, one such seedling producing fruit with especially desirable characteristics was selected for reproduction and commercialization.

ASEXUAL REPRODUCTION OF THE VARIETY

Our new nectarine tree was asexually reproduced by budding, as performed by us in the experimental orchard located near Modesto, Calif. and shows that all tree and fruit characteristics run true to the original tree and are identical in all respects.

SUMMARY OF THE VARIETY

The present new and distinct variety of nectarine tree is of large size, vigorous, upright growth and a regular and productive bearer of large, firm, white flesh, freestone fruit with good storage and shipping quality. The fruit is further characterized by being sub-acid, mild and sweet with excellent flavor and eating quality. Its firm flesh allows the fruit to be handled with the same procedure and equipment used to handle yellow flesh nectarines which is unique for a white flesh variety.

DESCRIPTION OF THE PHOTOGRAPHS

The accompanying photographic reproductions show typical specimens of the fruit and foliage of the new nectarine variety. The upper and lower surface of the leaves are illustrated, the exterior and sectional view of the fruit divided in the suture plane reveal flesh coloration and a stone remaining in place. The photographs were taken shortly after being picked (firm ripe) and the colors are as nearly true as is reasonably possible in a color representation of this type.

DESCRIPTION OF THE VARIETY

The following is a detailed botanical description of the new and distinct variety of nectarine tree, its flowers, foliage and fruit as based on observations of specimens grown in the experimental orchard near Modesto, Calif., with color terminology (except those in common terms) in accordance with Reinhold color Atlas by A. Kornerup and J. H. Wanscher.

Tree:
- *Size.*—Large.
- *Vigor.*—Vigorous.
- *Growth.*—Upright.
- *Density.*—Medium dense.
- *Shape.*—Usually pruned to vase shape.
- *Production.*—Productive.
- *Bearer.*—Regular.

Trunk:
- *Size.*—Medium stocky.
- *Texture.*—Medium shaggy.
- *Color.*—Brown to grayish brown.

Branches:
- *Size.*—Medium to stocky.
- *Surface.*—Smooth to medium rough.
- *Lenticels.*—Numerous. Medium size.
- *Color.*—Brown to reddish brown.

Leaves:
- *Size.*—Large. Average length — 6". Average width — 1½".
- *Form.*—Lanceolate. Pointed.
- *Thickness.*—Medium.
- *Texture.*—Smooth.
- *Petiole.*—Medium length. Medium thickness.
- *Margin.*—Crenate.
- *Glands.*—Reinform. Average number 2. Number varies from 1 to 4. Medium size. Located on base of leave blade and upper portion of petiole.
- *Color.*—Upper surface — green to deep green (28-E-8) to (28-F-8). Lower surface — light green to grayish green (28-C-7) to (28-D-7).

Flower buds:
- *Size.*—Medium.
- *Length.*—Medium.
- *Form.*—Plump.

Flowers:
- *Size.*—Large — showy.
- *Pollen.*—Present.
- *Color.*—Pink.

*Blooming period.*—Mar. 2, 1990 to Mar. 9, 1990. Varies slightly with climatic conditions.

Fruit:

*Maturity when described.*—Firm ripe.

*Date of first picking.*—Jul. 1, 1990.

*Date of last picking.*—Jul. 7, 1990.

*Size.*—Large. Average diameter axially — $2\frac{5}{8}''$ to $2\frac{7}{8}''$. Average transversely in suture plane — $2\frac{5}{8}''$ to $2\frac{7}{8}''$.

*Form.*—Globose — nearly symmetrical.

*Suture.*—Shallow — extends from base to apex.

*Base.*—Retuse.

*Apex.*—Rounded to slight depression.

*Cavity.*—Rounded to slightly elongated in suture plane. Average depth — $\frac{1}{2}''$. Average breadth — $\frac{7}{8}''$.

Flesh:

*Color.*—White with pale red streaks bleeding from pit cavity (8-A-1) to (8-A-3). Pit cavity pale red to light red (8-A-3) to (8-A-6) with some red streaks extending from pit cavity outward toward the skin.

*Texture.*—Firm, meaty.

*Fibers.*—Few, tender.

*Ripens.*—Evenly.

*Flavor.*—Excellent, sub-acid, mild and sweet.

*Juice.*—Moderate.

*Aroma.*—Moderate.

*Eating quality.*—Excellent.

*Amygdalin.*—Undetected.

Skin:

*Thickness.*—Medium to tough.

*Texture.*—Medium — tenacious to the flesh.

*Tendency to crack.*—None.

*Color.*—Chalk white to pale yellow ground color (3-A-1) to (3-A-2). Overspread with madder red to medium red (10-B-7) to (10-D-8) leaving a mottled red skin color where ground color appears at the skin surface.

Stone:

*Type.*—Freestone.

*Size.*—Medium to large. Average length — $1\frac{1}{4}''$. Average width — $\frac{7}{8}''$. Average thickness — $\frac{1}{2}''$.

*Form.*—Ovid.

*Base.*—Mostly straight — some rounded.

*Apex.*—Acuminate.

*Sizes.*—Equal to unequal.

*Surface.*—Irregularly furrowed toward apex, pitted toward base.

*Ridges.*—Rounded.

*Tendency to split.*—Very slight.

*Color.*—Brown to reddish brown (9-D-6) to (10-D-6).

Use: Dessert.

*Market.*—Local and long distant.

Keeping quality: Good.

Shipping quality: Good.

The new and distinct variety of nectarine tree, its flowers and fruit described above may vary slightly in detail due to cultural practices, soil types and climatic conditions under which the variety may be grown; the present description is that of the variety grown under the ecological conditions prevailing near Modesto, Calif.

We claim:

1. A new and distinct variety of nectarine tree, substantially as illustrated and described, which is of large size, vigorous upright in growth and a heavy and regular bearer of white flesh, freestone fruit with firm flesh that can be handled without excessive bruising in the same procedure and with the packing equipment used to handle yellow flesh nectarines; the fruit is further characterized by having excellent flavor and eating quality and the ability to be shipped to long distance markets.

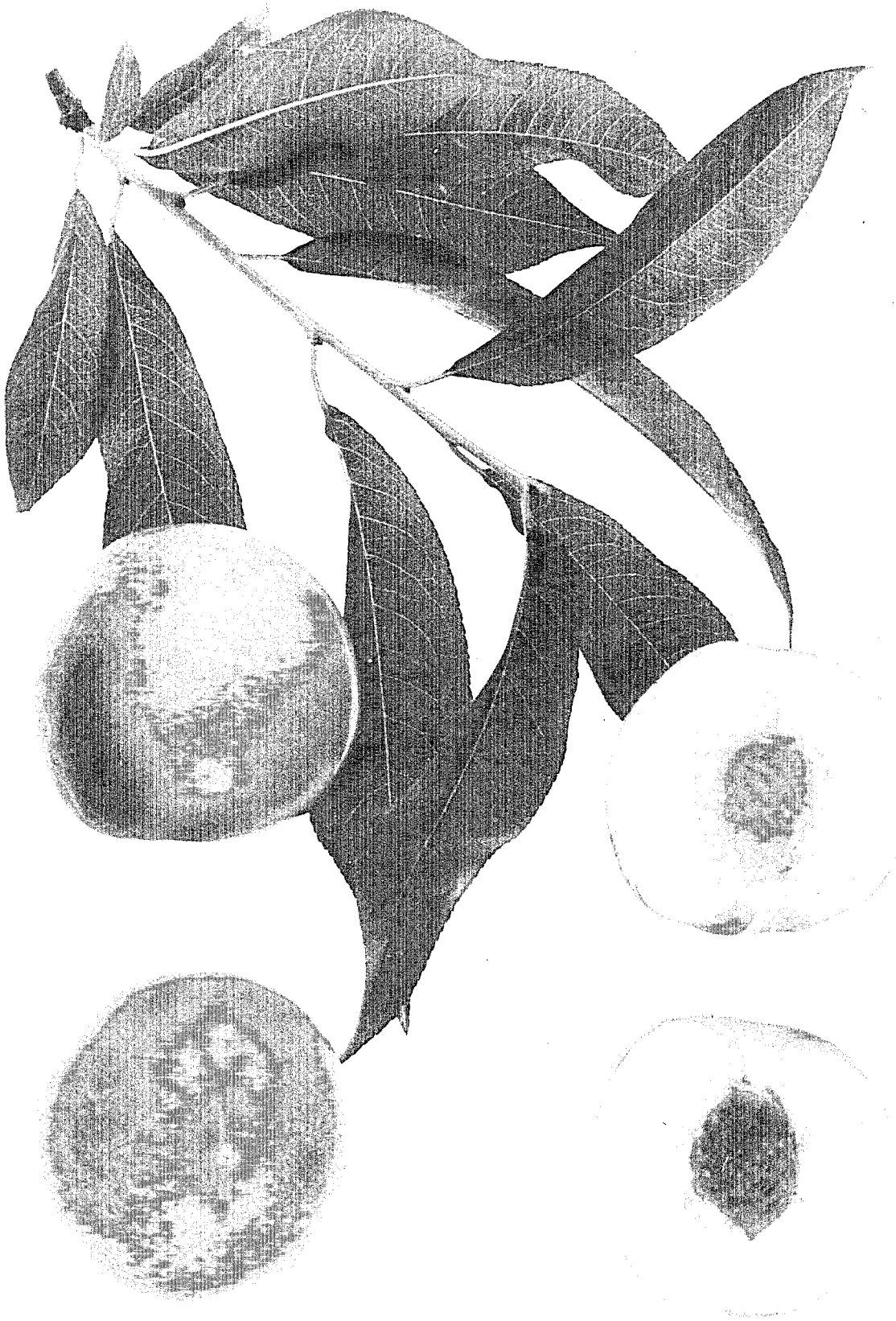

* * * * *